(12) United States Patent
Schafer

(10) Patent No.: US 6,418,189 B1
(45) Date of Patent: Jul. 9, 2002

(54) EXPLOSIVE MATERIAL DETECTION APPARATUS AND METHOD USING DUAL ENERGY INFORMATION OF A SCAN

(75) Inventor: David A. Schafer, Rowley, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 09/491,481

(22) Filed: Jan. 24, 2000

(51) Int. Cl.$^7$ .............................................. G01N 23/04
(52) U.S. Cl. .......................................... 378/57; 378/88
(58) Field of Search ............................ 378/57, 88, 51, 378/53, 54, 86, 89, 90

(56) References Cited

U.S. PATENT DOCUMENTS

| | | | |
|---|---|---|---|
| 4,029,963 A | * | 6/1977 | Alvarez et al. .............. 250/360 |
| 5,642,393 A | * | 6/1997 | Krug et al. .................... 378/57 |
| 5,661,774 A | | 8/1997 | Gordon et al. ............... 378/101 |

OTHER PUBLICATIONS

R. Alvarez et al., "Energy–selective Reconstructions in X–ray Computerized Tomography," Phys. Med. Biol., 1976, vol. 21, No. 5, 733–744.
W. Marshall et al., "Initial Results with Prereconstruction Dual–Energy Computed Tomography (PREDECT)'," Radiology, vol. 140, No. 2, pp. 421–430, Aug. 1981.
J.P. Stonestrom et al., "Framework for Spectral Artifact Correction in X–Ray CT," IEEE Transactions on Biomedical Engineering, vol. BME–28, No. 2, Feb. 1981, pp. 128–141.

* cited by examiner

Primary Examiner—Robert H. Kim
Assistant Examiner—Courtney Thomas
(74) Attorney, Agent, or Firm—McDermott, Will & Emery

(57) ABSTRACT

An apparatus and method for detecting explosive material uses dual energy information of an X-ray scan of the material. The object in question is located within a region which includes extraneous objects. The region is scanned by an X-ray radiation source which alternately emits radiation at two different energy levels, and a detector array collects the radiation after passing through the material. A reconstruction computer generates a CT image from the series of projections corresponding to one of the two energy levels. A spatial analysis computer analyzes the CT image and determines the projection which includes only the object in question (a clear-path projection) or the projection which includes the object in question along with the fewest extraneous objects. A projection computer uses the high energy clear-path projection and the low energy clear-path projection to determine quantitative information relating to two physical characteristics of the object in question, for example atomic number and density. The quantitative information is used to distinguish explosive materials from non-explosive materials.

20 Claims, 8 Drawing Sheets

EXPLOSIVE MATERIAL DETECTION APPARATUS AND METHOD USING DUAL ENERGY INFORMATION OF A SCAN

CROSS-REFERENCE TO RELATED APPLICATIONS

Not Applicable

STATEMENT REGARDING FEDERALLY SPONSORED RESEARCH

Not Applicable

REFERENCE TO MICROFICHE APPENDIX

Not Applicable

FIELD OF THE INVENTION

The present invention relates to methods and systems for detecting explosive materials, and more particularly, to methods and systems for detecting explosive materials which analyze X-ray radiation transmission and scattering to determine one or more physical characteristics of a material.

BACKGROUND OF THE INVENTION

Various X-ray baggage scanning systems are known for detecting the presence of explosives and other prohibited items in baggage, or luggage, prior to loading the baggage onto a commercial aircraft. A common technique of measuring a material's density is to expose the material to X-rays and to measure the amount of radiation absorbed by the material, the absorption being indicative of the density. Since many explosive materials may be characterized by a range of densities differentiable from that of other items typically found in baggage, explosives are generally amenable to detection by X-ray equipment.

Most X-ray baggage scanning systems in use today are of the "line scanner" type and include a stationary X-ray source, a stationary linear detector array, and a conveyor belt for transporting baggage between the source and detector array as the baggage passes through the scanner. The X-ray source generates an X-ray beam that passes through and is partially attenuated by the baggage and is then received by the detector array. During each measuring interval the detector array generates data representative of the integral of density of the planar segment of the baggage through which the X-ray beam passes, and this data is used to form one or more raster lines of a two-dimensional image. As the conveyor belt transports the baggage past the stationary source and detector array, the scanner generates a two-dimensional image representative of the density of the baggage, as viewed by the stationary detector array. The density image is typically displayed for analysis by a human operator.

Techniques using dual energy X-ray sources are known for providing additional information about a material's characteristics, beyond solely a density measurement. Techniques using dual energy X-ray sources involve measuring the X-ray absorption characteristics of a material for two different energy levels of X-rays. Depending upon the calibration of the scanner, dual energy measurements provide an indication of dual parameters of the material being scanned; for example, at one calibration setting, the dual parameters can be chosen to be the material's atomic number and the material's density. At another calibration setting, the dual parameters can be chosen to be the material's Photoelectric coefficients and the material's Compton coefficients. At yet another calibration setting, the dual parameters can be chosen to be an amount of a first material present (e.g., steel) and an amount of a second material present (e.g., aluminum). Dual energy X-ray techniques for energy-selective reconstruction of X-ray Computer Tomography (hereinafter referred to as CT) images are described, for example, in Robert E. Alvarez and Albert Macovski, "Energy-selective Reconstructions in X-ray Computerized Tomography", Phys. Med. Biol. 1976, Vol. 21, No. 5, 733–744; and U.S. Pat. Nos. 4,029,963 and 5,132,998. One algorithm used to generate such dual parameters from dual energy X-ray projection data is known as the Alvarez/Macovski Algorithm (hereinafter referred to as AMA).

One proposed use for such dual energy techniques has been in connection with a baggage scanner for detecting the presence of explosives in baggage. Explosive materials are generally characterized by a known range of atomic numbers and are therefore amenable to detection by such dual energy X-ray sources. One such dual energy source is described in copending U.S. patent application Ser. No. 08/671,202, entitled "Improved Dual Energy Power Supply," which is assigned to the same assignee as the present invention and which is incorporated herein in its entirety by reference.

Plastic explosives present a particular challenge to baggage scanning systems because, due to their moldable nature, plastic explosives may be formed into geometric shapes that are difficult to detect. Most explosives capable of significantly damaging an aircraft weigh at least a pound and are sufficiently large in length, width, and height so as to be readily detectable by an X-ray scanner system regardless of the explosive's orientation within the baggage. However, a plastic explosive powerful enough to damage an aircraft may be formed into a relatively thin sheet that is extremely small in one dimension and is relatively large in the other two dimensions. The detection of plastic explosives may be difficult because it may be difficult to see the explosive material in the image, particularly when the material is disposed so that the thin sheet is parallel to the direction of the X-ray beam as the sheet passes through the system.

Thus, detection of suspected baggage requires very attentive operators. The requirement for such attentiveness can result in greater operator fatigue, and fatigue as well as any distractions can result in a suspected bag passing through the system undetected.

Accordingly, a great deal of effort has been made to design a better baggage scanner. Such designs, for example, have been described in U.S. Pat. No. 4,759,047 (Donges et al.); U.S. Pat. No. 4,884,289 (Glockmann et al.); U.S. Pat. No. 5,132,988 (Tsutsui et al.); U.S. Pat. No. 5,182,764 (Peschmann et al.); U.S. Pat. No. 5,247,561 (Kotowski); U.S. Pat. No. 5,319,547 (Krug et al.); U.S. Pat. No. 5,367,552 (Peschmann et al.); U.S. Pat. No. 5,490,218 (Krug et al.) and German Offenlegungsschrift DE 31 503 06 A1 (Heimann GmbH).

At least one of these designs, described in U.S. Pat. No. 5,182,764 (Peschmann et al.) and U.S. Pat. No. 5,367,552 (Peschmann et al.) (hereinafter the '764 and '552 patents), has been commercially developed and is referred to hereinafter as the "Invision Machine." The Invision Machine includes a CT scanner of the third generation type, which typically includes an X-ray source and an X-ray detector system secured respectively to diametrically opposite sides of an annular-shaped platform or disk. The disk is rotatably mounted within a gantry support so that in operation the disk continuously rotates about a rotation axis while X-rays pass from the source through an object positioned within the opening of the disk to the detector system.

The detector system can include a linear array of detectors disposed as a single row in the shape of a circular arc having a center of curvature at the focal spot of the X-ray source, i.e., the point within the X-ray source from which the X-rays emanate. The X-ray source generates a fan shaped beam, or fan beam, of X-rays that emanates from the focal spot, passes through a planar imaging field, and is received by the detectors. The CT scanner includes a coordinate system defined by X-, Y- and Z-axes, wherein the axes intersect and are all normal to one another at the center of rotation of the disk as the disk rotates about the rotation axis. This center of rotation is commonly referred to as the "isocenter." The Z-axis is defined by the rotation axis and the X- and Y-axes are defined by and lie within the planar imaging field. The fan beam is thus defined as the volume of space defined between a point source, i.e., the focal spot, and the receiving surfaces of the detectors of the detector array exposed to the X-ray beam. Because the dimension of the receiving surfaces of the linear array of detectors is relatively small in the Z-axis direction the fan beam is designed to be relatively thin in the Z-axis direction. Each detector generates an output signal representative of the intensity of the X-rays incident on that detector. Since the X-rays are partially attenuated by all the mass in their path, the output signal generated by each detector is representative of the density of all the mass disposed in the imaging field between the X-ray source and that detector.

As the disk rotates, the detector array is periodically sampled, and for each measuring interval each of the detectors in the detector array generates an output signal representative of the density of a portion of the object being scanned during that interval. The collection of all of the output signals generated by all the detectors in a single row of the detector array for any measuring interval is referred to as a "projection," or equivalently as a "view," and the angular orientation of the disk (and the corresponding angular orientations of the X-ray source and the detector array) during generation of a projection is referred to as the "projection angle." At each projection angle, the path of the X-rays from the focal spot to each detector, called a "ray," increases in cross section from a point source to the receiving surface area of the detector, and thus is thought to magnify the density measurement because the receiving surface area of the detector area is larger than any cross sectional area of the object through which the ray passes.

As the disk rotates around the object being scanned, the scanner generates a plurality of projections at a corresponding plurality of projection angles. Using well known algorithms a CT image of the object may be generated from all the projection data collected at each of the projection angles. The CT image is representative of the density of a two dimensional "slice" of the object through which the fan beam has passed during the rotation of the disk through the various projection angles. The resolution of the CT image is determined in part by the width of the receiving surface area of each detector in the plane of the fan beam, the width of the detector being defined herein as the dimension measured in the same direction as the width of the fan beam, while the length of the detector is defined herein as the dimension measured in a direction normal to the fan beam parallel to the rotation or Z-axis of the scanner. In general, the resolution of the CT image is inversely proportional to the width of the receiving surface of each detector in the plane of the fan beam.

FIGS. 1, 2 and 3 show perspective, end cross-sectional and radial cross-sectional views, respectively, of a typical baggage scanning system 100, which includes a conveyor system 110 for continuously conveying baggage or luggage 112 in a direction indicated by arrow 114 through a central aperture of a CT scanning system 120. The conveyor system includes motor driven belts for supporting the baggage. Conveyer system 110 is illustrated as including a plurality of individual conveyor sections 122; however, other forms of conveyor systems may be used.

The CT scanning system 120 includes an annular shaped rotating platform, or disk, 124 disposed within a gantry support 125 for rotation about a rotation axis 127 (shown in FIG. 3) that is preferably parallel to the direction of travel 114 of the baggage 112. Disk 124 is driven about rotation axis 127 by any suitable drive mechanism, such as a belt 116 and motor drive system 118, or other suitable drive mechanism, such as the one described in U.S. Pat. No. 5,473,657 issued Dec. 5, 1995 to Gilbert McKenna, entitled "X-ray Tomographic Scanning System," which is assigned to the present assignee and which is incorporated herein in its entirety by reference. Rotating platform 124 defines a central aperture 126 through which conveyor system 110 transports the baggage 112.

The system 120 includes an X-ray tube 128 and a detector array 130 which are disposed on diametrically opposite sides of the platform 124. The detector array 130 can be a two-dimensional array such as the array described in a U.S. patent application Ser. No. 08/948,450 entitled, "Area Detector Array for Computed Tomography Scanning System," of common assignee, and incorporated herein in its entirety by reference. The system 120 further includes a data acquisition system (DAS) 134 for receiving and processing signals generated by detector array 130, and an X-ray tube control system 136 for supplying power to, and otherwise controlling the operation of, X-ray tube 128. The system 120 is also preferably provided with a computerized system (not shown) for processing the output of the data acquisition system 134 and for generating the necessary signals for operating and controlling the system 120. The computerized system can also include a monitor for displaying information including generated images. System 120 also includes shields 138, which may be fabricated from lead, for example, for preventing radiation from propagating beyond gantry 125.

The X-ray tube 128 may generate a pyramidically shaped beam, often referred to as a "cone beam," 132 of X-rays that pass through a three dimensional imaging field, through which conveying system 110 transports baggage 112. After passing through the baggage disposed in the imaging field, detector array 130 receives cone beam 132 and generates signals representative of the densities of exposed portions of baggage 112. The beam therefore defines a scanning volume of space. Platform 124 rotates about its rotation axis 127, thereby transporting X-ray source 128 and detector array 130 in circular trajectories about baggage 112 as the conveyor system 110 continuously transports baggage through central aperture 126, so as to generate a plurality of projections at a corresponding plurality of projection angles.

Pre-reconstruction analysis, post-reconstruction analysis and multiple projection/non-CT analysis are three prior art techniques generally recognized for using dual energy X-ray sources in materials analysis (e.g., in a baggage scanner for detecting the presence of explosives in baggage). In pre-reconstruction analysis, the signal flow is as shown in FIG. 4. The scanner 120 is typically similar to the one shown in FIG. 1 and has an X-ray source capable of producing a fan beam at two distinct energy levels (i.e., dual energy). The DAS 134 gathers signals generated by detector array (130 in FIG. 1; not shown in FIG. 4) at discrete angular positions of the rotating platform (124 in FIG. 1; not shown in FIG. 4), and passes the signals to the pre-processing element 206. The pre-processing element 206 re-sorts the data it receives from the DAS 134 in order to optimize the sequence for the subsequent mathematical processing. The pre-processing element 206 also corrects the data from the DAS 134 for detector temperature, intensity of the primary beam, gain and offset, and other deterministic error factors. Finally, the pre-processing element 206 extracts data corresponding to high-energy views and routes it to a high energy channel path 208, and routes the data corresponding to low-energy views to a low energy path 210. The projection computer 212 receives the projection data on the high energy path 208 and the low energy path 210 and performs Alvarez/Macovski Algorithm processing to produce a first stream of projection data 214 which is dependent on a first parameter of the material being scanned and a second stream of projection data 216 which is dependent on a second parameter of the material scanned. The first parameter is often the atomic number and the second parameter is often material density, although other parameters may be selected. A first reconstruction computer 218 receives the first stream of projection data 214 and generates a CT image from the series of projections corresponding to the first material parameter. A second reconstruction computer 220 receives the second stream of projection data 216 and generates a CT image from the series projections corresponding to the second material parameter.

In post-reconstruction analysis, the signal flow is as shown in FIG. 5. As is described herein for pre-processing analysis, a pre-processing element 206 receives data from a DAS 134, performs several operations upon the data, then routes the data corresponding to high-energy views to a high energy path 208 and routes the data corresponding to low-energy views to a low energy path 210. A first reconstruction computer 218 receives the projection data from the high-energy path 208 and generates a CT image corresponding to the high-energy series of projections. A second reconstruction computer 220 receives the projection data from the low-energy path 210 and generates a CT image corresponding to the low-energy series of projections. A projection computer 212 receives the high energy CT data 222 and the low-energy CT data 224 and performs AMA processing to produce CT data 226 which is dependent on a first parameter of the material being scanned and a second stream of projection data 228 which is dependent on a second parameter of the material scanned.

In multiple projection/non-CT analysis, the signal flow is as shown in FIG. 6. As is described herein for pre-processing analysis, a pre-processing element 206 receives data from a DAS 134, performs several operations upon the data, then routes the data corresponding to high-energy views to a high energy path 208 and routes the data corresponding to low-energy views to a low energy path 210. A projection computer 212 receives the high energy projection views and the low-energy projection views via a data selection device 230, and performs AMA processing to produce a first stream of projection data 214 which is dependent on a first parameter of the material being scanned and a second stream of projection data 216 which is dependent on a second parameter of the material scanned. The data selection device 230 selects projection data corresponding to a number of particular views in response to commands from a spatial computer 232. The spatial computer 232 utilizes a variety of system parameters to determine which views should be selected. Unlike the pre and post-reconstruction analysis, multiple projection/non-CT analysis requires only a small number of projections from the scanning system 120. Because a full CT reconstruction is never performed, this analysis technique does not require the full range of projection angles available. The reduced number of projections and the lack of CT analysis significantly reduces the computational load of the system. However, this technique is not reliable for bomb detection applications unless the explosive material is the only object in the projection path. This technique works especially well if in addition to being the only object in the path, the thickness of the object is known and available to the detection algorithm. In prior art systems, a great deal of effort is expended to determine which of a small number of projections provides a clear, optimum view of the suspected explosive object, free from overlying non-explosive materials.

It is an object of the present invention to substantially overcome the above-identified drawbacks of the prior art.

It is a further object of this invention to provide a system for detecting explosive materials which reduces the computational load typical of prior art CT systems.

It is another object of this invention to provide a system for detecting explosive materials which increases the reliability of selecting a clear, optimum view of a suspected explosive object.

SUMMARY OF THE INVENTION

The present invention is directed to a method and system for detecting explosive materials using dual energy information of a scan. The object to be detected has at least two measurable physical characteristics, for example atomic number and density, and is located in a region defined at least by a longitudinal axis. The first step of the method is to scan the region to generate scan data representative of the region. The scanning is accomplished by providing a radiation source which is capable of alternately radiating at least at two power levels, and an array of detectors on opposed sides of the region. The radiation source is then rotated about the longitudinal axis while the radiation source emits radiation toward the array of detectors. The array of detectors receive radiation from the region to generate scan data at each power level for the region.

The second step of the method is to define at least one image data slice corresponding to a plurality of positions along the longitudinal axis of the region. Each of said image data slices defines a plurality of scan data projections obtained from a respective plurality of view angles during the scanning step, where each scan data projection contains scan data at its respective view angle.

The third step of the method is to select at least one clear-path scan data projection from the image data slice, and to select a first set of scan data at the first energy level and a second set of scan data at said second energy level, each set of data corresponding to said clear-path projection. The clear-path projection includes at least the object to be detected.

The fourth step of the method is to generate, from the first and second sets of scan data, a first value representative of the first physical characteristic and a second value representative of the second physical characteristic.

The fifth and final step of the method is to recognize and identify the object as a function of said first value and said second value.

In accordance with one preferred embodiment of the invention, the clear-path projection further includes only the object to be detected; the set of scan data for that projection does not include any information corresponding to other objects within the region.

In another embodiment, the step of generating the two values, each of which corresponds to a particular physical characteristic of the object, further includes processing the first and second sets of scan data with a computer system programmed to execute the Alvarez/Macovski algorithm. The result of such processing of the first and second sets of scan data is to produce a first value corresponding to a first physical characteristic of the object, for example the atomic number, and a second value corresponding to a second physical characteristic, for example the density of the object.

In yet another embodiment, the method of the invention further includes selecting a second clear-path projection of the object.

In still another embodiment of the invention, the step of selecting at least one clear-path scan data projection from the image data slice may further include the step of determining the linear dimension (i.e., the thickness) of the material being scanned along an axis defined by the beam path between the X-ray source and the detector array when the rotating platform is situated at the clear-path angle. The linear dimension of the material along this axis may be used as a parameter in determining the values representative of the first and second physical characteristics.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE INVENTION

Figure 7:
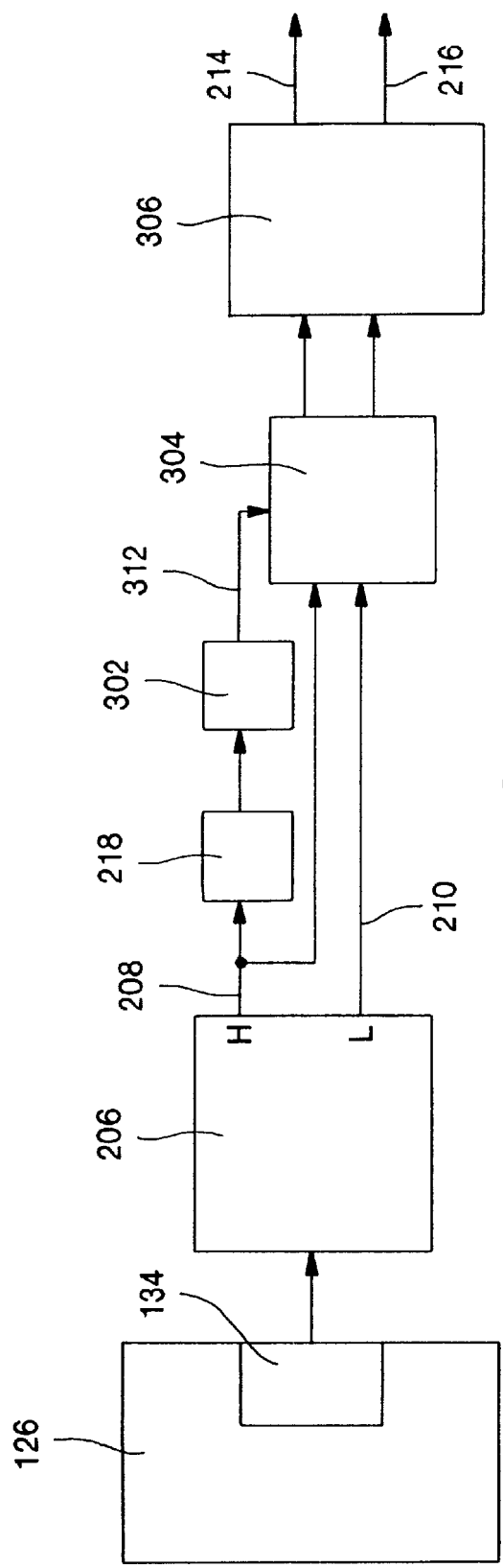
FIG. 7 shows a signal flow diagram of an explosive detection system constructed according to the present invention; and, FIG. 8 shows a signal flow diagram of the explosive material detection system with a material analysis computer.

The present invention is directed to an explosive detection system using dual energy information of a scan. In particular, the invention determines certain characteristics and physical parameters of a material under examination generated by a relatively small number of high and low energy projective views from an X-ray scanner as was described herein for multiple projection/non-CT analysis, but uses spatial information from a CT reconstruction of either a set of high energy projections or a set of low energy projections to select the best views. FIG. 7 shows the signal flow according to one embodiment of the present invention.

Figure 1:
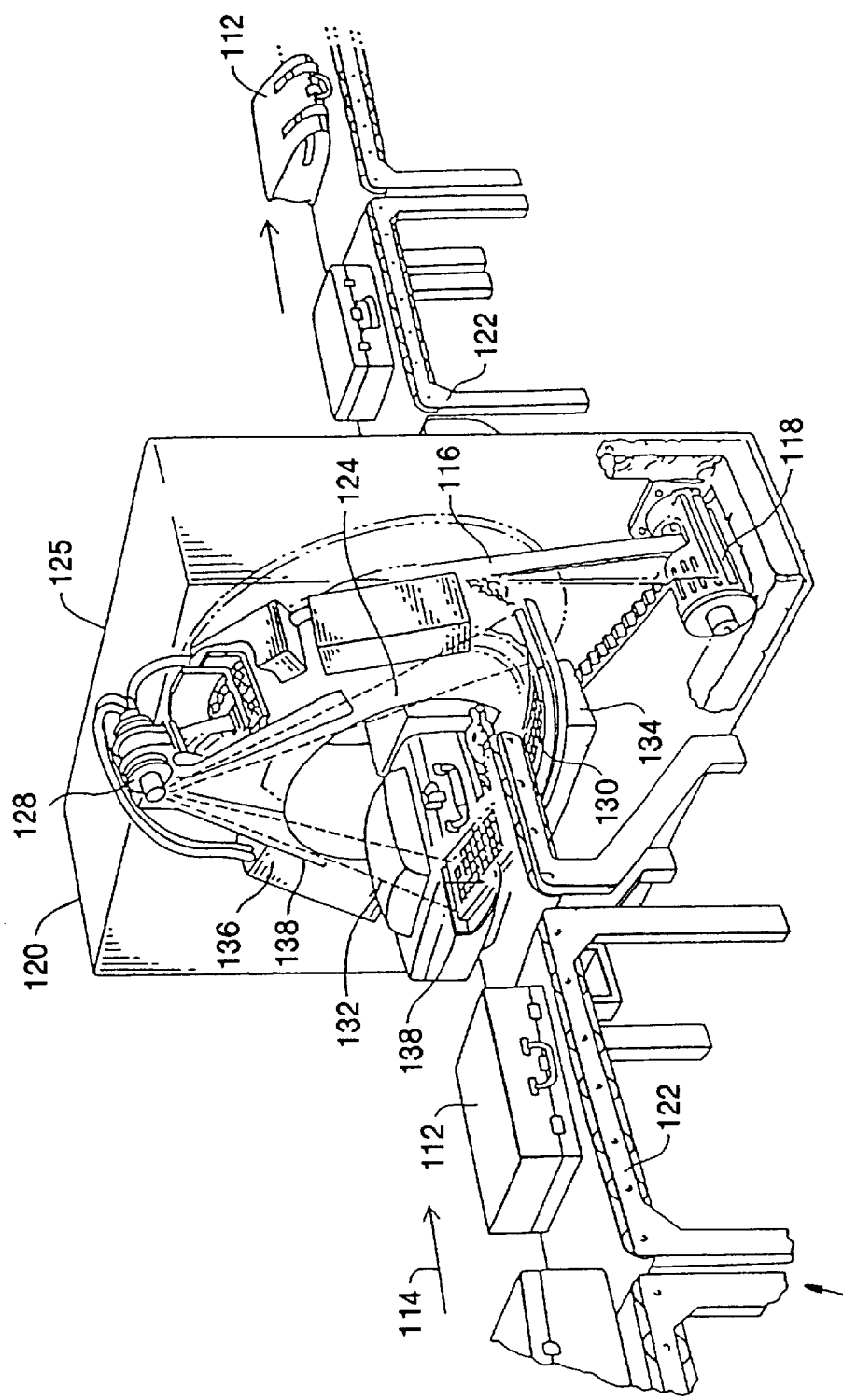
FIG. 1 shows a perspective view of a baggage scanning system in accordance with the present invention.
Figure 2:
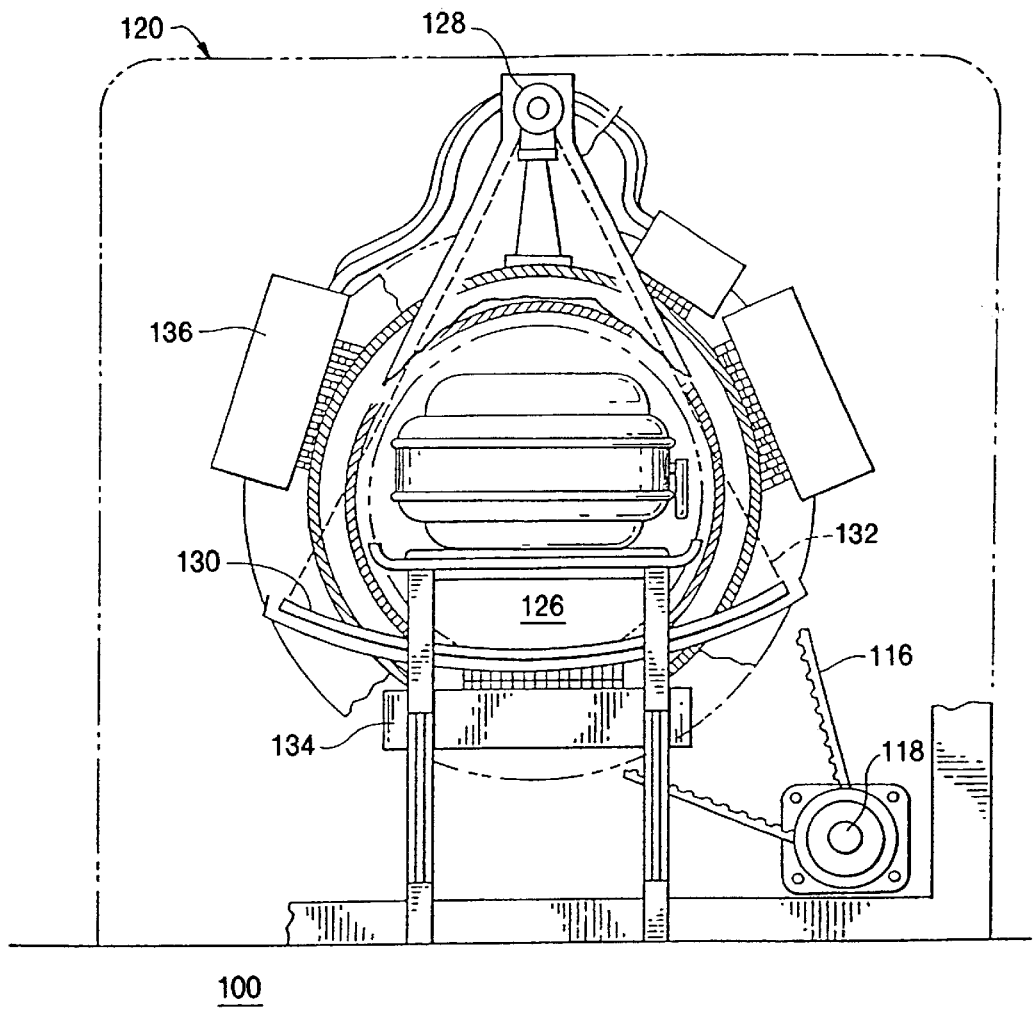
FIG. 2 shows a cross-sectional end view of the system shown in FIG. 1.
Figure 3:
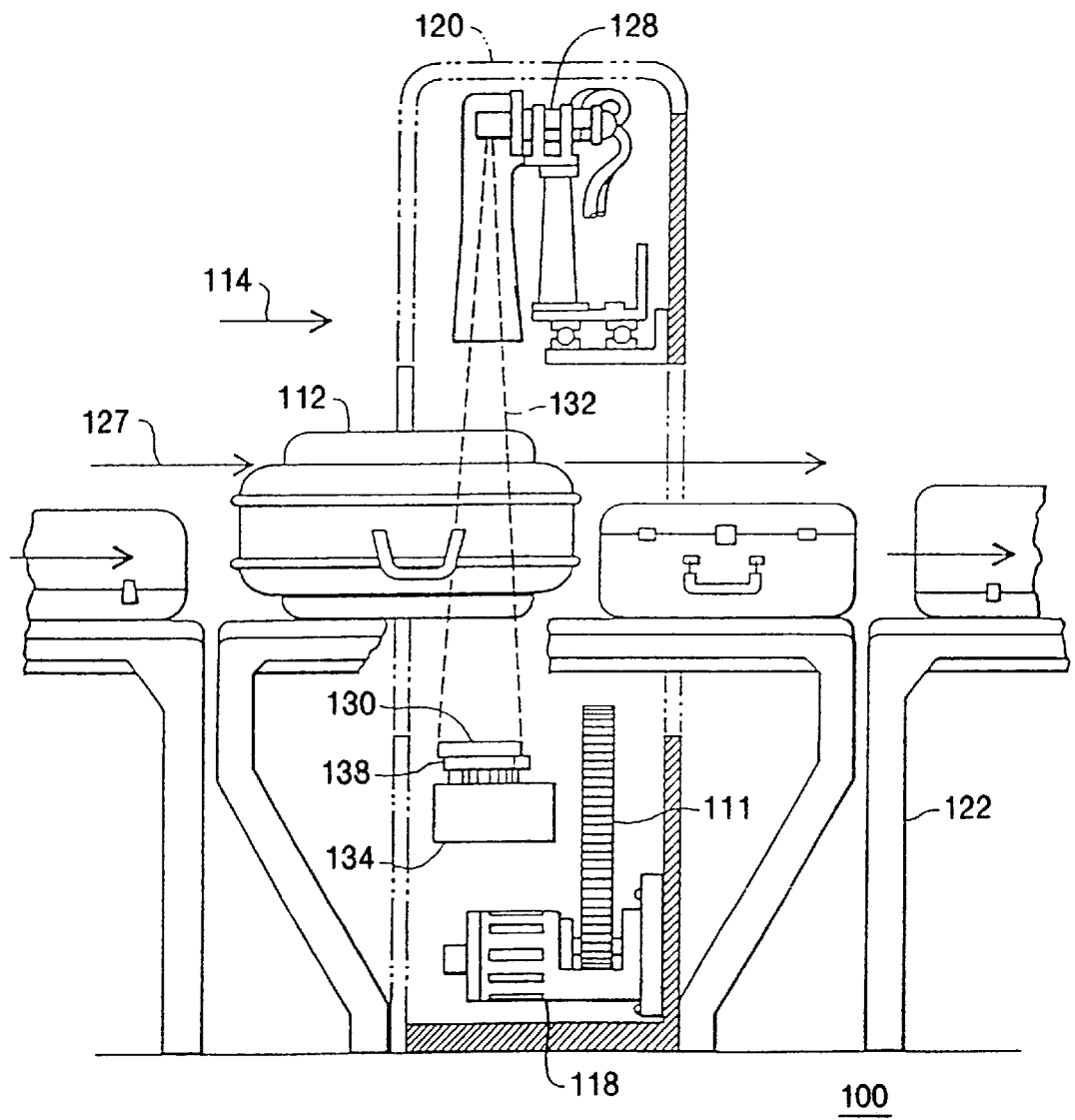
FIG. 3 shows a cross-sectional radial view of the system shown in FIG. 1.
Figure 4:
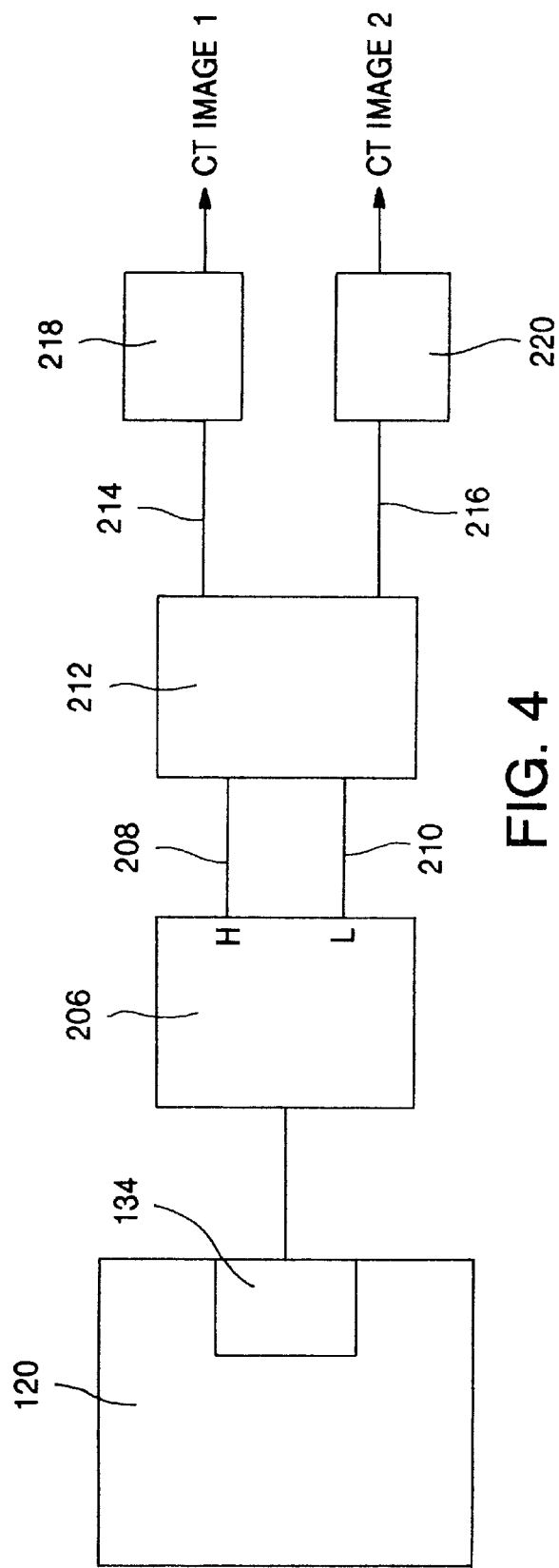
FIG. 4 shows a signal flow diagram of a system capable of performing pre-reconstruction analysis.
Figure 5:
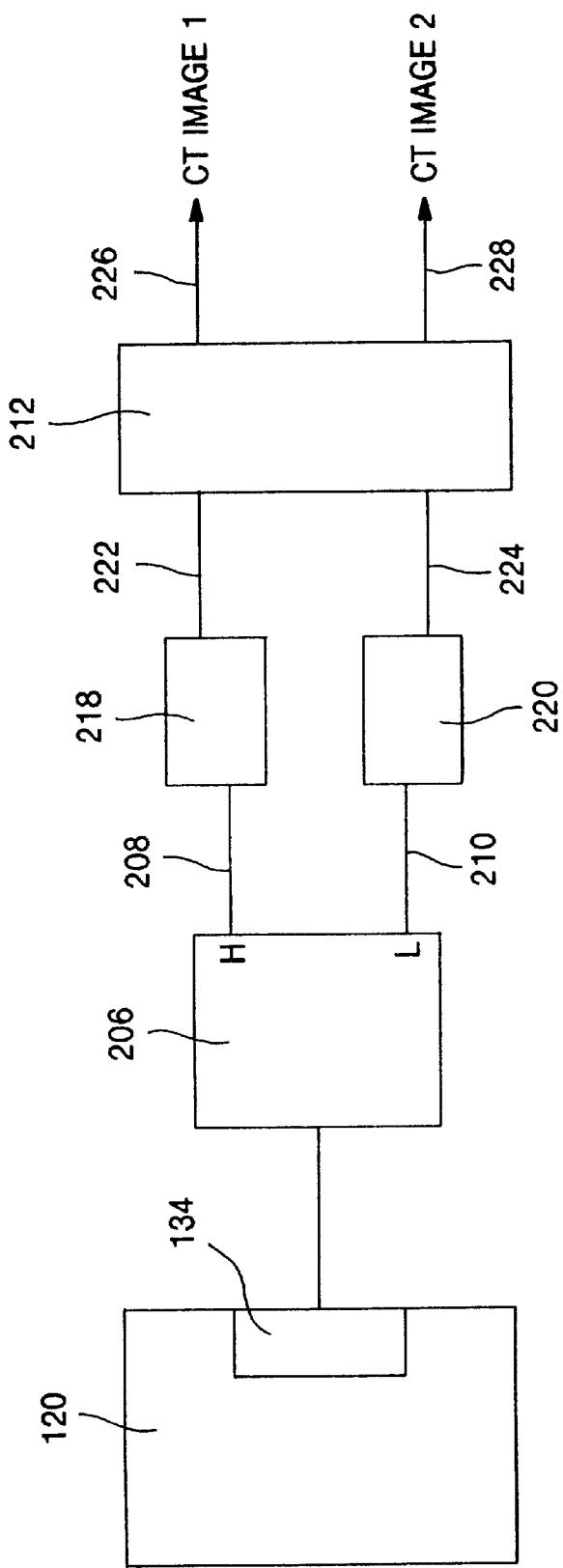
FIG. 5 shows a signal flow diagram of a system capable of performing post-reconstruction analysis.

As is described herein for pre-processing analysis, a DAS 134 gathers signals generated by detector array (130 in FIG. 1; not shown in FIG. 7) at discrete angular postions of the rotating platform (124 in FIG. 1; not shown in FIG. 7) the rotation axis (127 in FIG. 1; not shown in FIG. 7), and passes these signals in the form of projection data to the pre-processor 206. The pre-processor 206 receives projection data from the DAS 134, performs several operations upon this data (described hereinbefore), then routes the pre-processed data corresponding to high-energy views to a data selection device 304 via a high energy path 208, and routes the pre-processed data corresponding to low-energy views to the data selection device 304 via low energy path 210. The pre-processor 206 also provides the pre-processed data corresponding to the high-energy views to a reconstruction computer 218 via high energy data path 208. The reconstruction computer 218 receives the pre-processed data from the high-energy path 208 and generates an image data slice (i.e., a CT image) corresponding to the high-energy series of projections about rotation axis 127. The reconstruction computer 218 provides the CT image to a spatial analysis computer 302, which receives and analyzes the CT image to determine the optimum projection angle or angles to view the object to be detected within the image. The spatial analysis computer 302 provides this optimum angular information via angle information path 312 to the data selection device 304, which selects the high energy and low energy data corresponding to the optimum projection angle and provides such data to the projection computer 306. The projection computer 306 receives the high energy projection data and the low-energy projection data, and performs AMA processing to produce a first stream of AMA projection data 214 which is dependent on a first parameter of the material being scanned, and a second stream of AMA projection data 216 which is dependent on a second parameter of the material being scanned.

Figure 6:
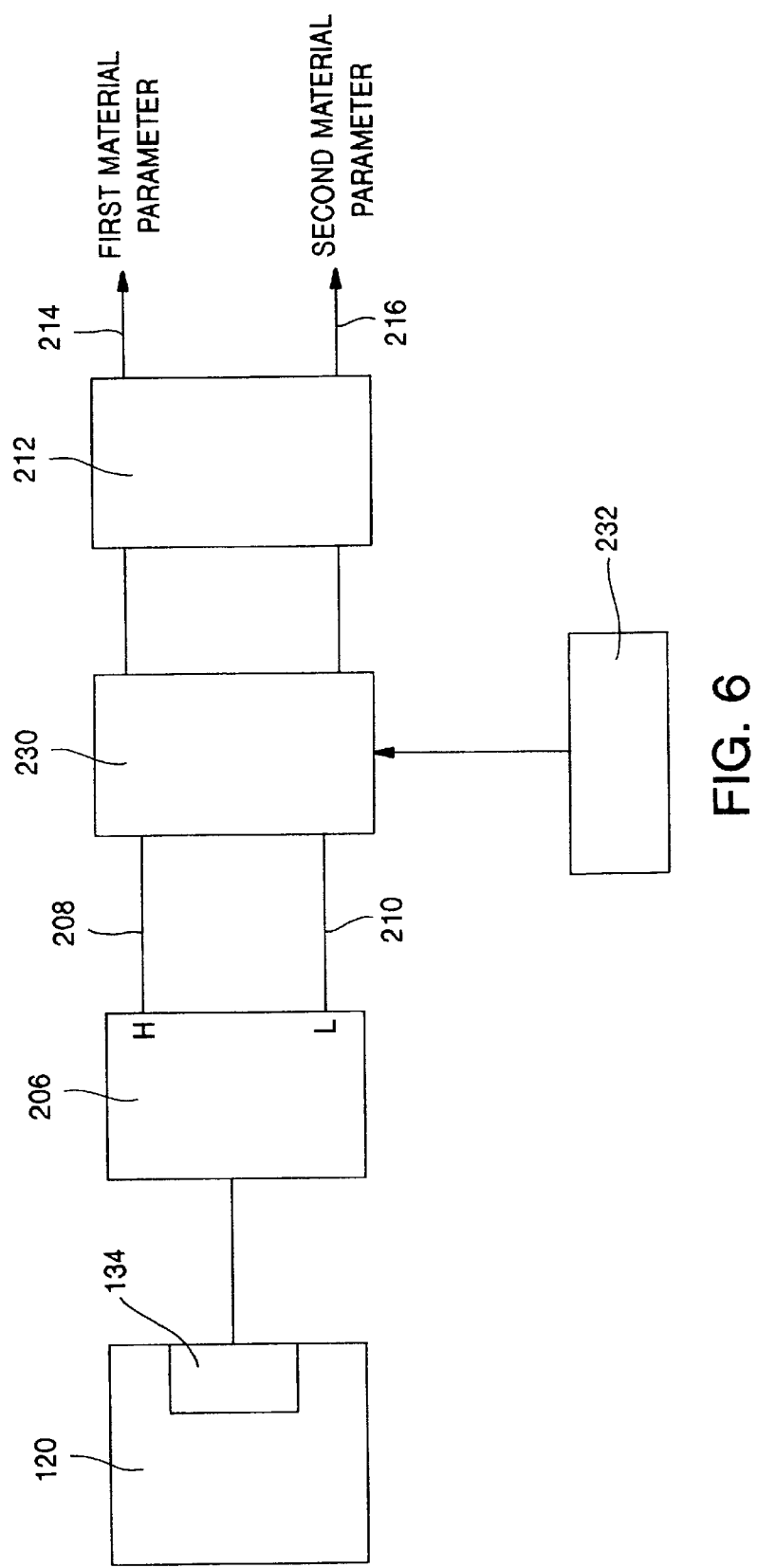
FIG. 6 shows a signal flow diagram of a system capable of performing multiple projection/non-CT analysis.

The invention shown in FIG. 7 is similar to the multiple projection/non-CT system shown in FIG. 6 in that the invention chooses a projection from a particular angle of rotating platform 124 about the rotation axis 127. As was explained hereinbefore, a high energy projection and a low energy projection from a single angular position of the rotating platform 124 will yield accurate parametric information about an object of interest, as long as no extraneous objects are situated in the beam path between the X-ray source and the detector array. The angle of the rotating platform which corresponds to such an optimum or clear-path projection is hereinafter referred to as the clear-path angle. The invention uses information from the CT image provided by the reconstruction computer 218 to select the projection which corresponds to the clear-path angle. Although the illustrated embodiment reconstructs a CT image from the data corresponding to the high-energy views, other embodiments of the invention may use data corresponding to low energy views, or some combination of the high energy data and the low energy data, to reconstruct a CT image for determination of the clearpath angle.

Figure 8:
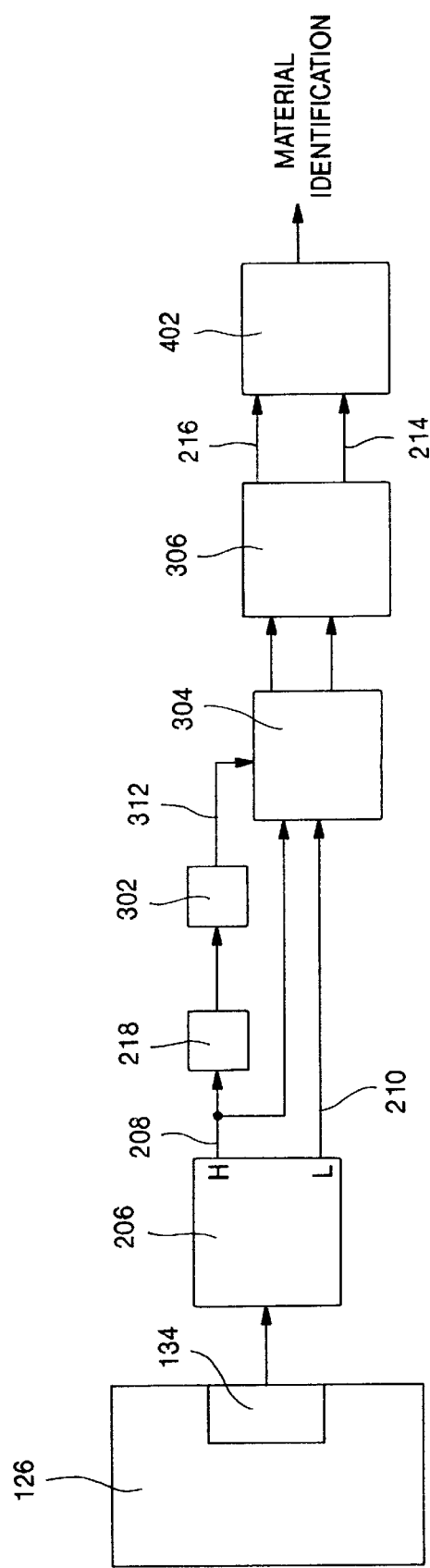

FIG. 8 shows a materials analysis computer 402 receiving AMA projection data from the system shown in FIG. 7. The materials analysis computer 402 receives the first stream of AMA projection data 214 which is dependent on a first parameter of the material being scanned, and a second stream of AMA projection data 216 which is dependent on a second parameter of the material being scanned. The materials analysis computer 402 uses this information regarding the two parameters of the material being scanned (for example, atomic number and density) to distinguish between explosive and non-explosive materials. The materials analysis computer 402 thus produces data corresponding to the identification of the material.

In another embodiment of the invention, the spatial analysis computer 302 may determine two or more clear-path projection angles and provide this multi-angular information to the data selection device 304 via angle information path 312. The data selection device 304 receives this multi-angular information and selects the high and low-energy view data corresponding to the clear-path projections indicated by the multi-angular information. The projection computer 306 receives the high energy projection data and the low-energy projection data, and performs AMA processing to produce a first stream of AMA projection data 214 which is dependent on a first parameter of the material being scanned, and a second stream of AMA projection data 216 which is dependent on a second parameter of the material being scanned.

In yet another embodiment of the invention, the spatial analysis computer 302 may also determine the linear dimension (i.e., the thickness) of the material being scanned along an axis defined by the beam path between the X-ray source and the detector array when the rotating platform is situated at the clear-path angle. The linear dimension of the material along this axis may be used by the projection computer 306 as a parameter of the AMA processing to further refine the determination of the first stream of AMA projection data 214 and the second stream of AMA projection data 216.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A method of detecting an object in a region having a longitudinal axis, said object having at least a first physical characteristic and a second physical characteristic, said method comprising:
   A. scanning said region to generate scan data representative of said region, said scanning comprising:
      i. providing a radiation source alternately radiating at least at a first energy level and at a second energy level, and an array of detectors on opposed sides of said region;
      ii. rotating at least said radiation source about said longitudinal axis while said radiation source emits radiation toward said array of detectors; and,
      iii. with said array of detectors, receiving radiation from said region to generate said scan data at said first energy level and said second energy level for said region;
   B. defining at least one image data slice, each data slice corresponding to a position along said longitudinal axis of said region, each of said image data slices defining a plurality of scan data projections obtained from a respective plurality of view angles during the scanning step, each scan data projection containing scan data at its respective view angle;
   C. generating a CT image from said scan data at said first energy level, and using the CT image to select at least one clear-path scan data projection from said image data slice, corresponding to one of said view angles, wherein said clear-path projection includes at least said object, and selecting a first set of scan data at said first energy level and a second set of scan data at said second energy level, each set of data corresponding to said clear-path projection;
   D. generating, from said first set of scan data and said second set of scan data, corresponding to said clear-path scan data projection, a first value representative of said first physical characteristic and a second value representative of said second physical characteristic, and recognizing and identifying said object as a function of said first value and said second value.

2. A method according to claim 1, wherein said clear-path projection includes only said object.

3. A method according to claim 1, wherein said step of generating said first value and said second value further includes the step of applying an Alvarez/Macovski algorithm to said first set of scan data and said second set of scan data by way of a computer system, so as to produce said first value and said second value.

4. A method according to claim 1, wherein said array of detectors is also rotated about said longitudinal axis to scan said region.

5. A method according to claim 1, further comprising selecting a second view angle for a second clear-path projection of said object, said second clear path projection being generated from said scan data generated during said scanning step.

6. A method according to claim 1, further comprising selecting a plurality of additional view angles for a plurality of additional clear-path projections of the object, said plurality of additional clear-path projections being generated from said scan data generated during said scanning step.

7. A method according to claim 1, wherein said region is scanned with a computed tomography (CT) device to generate said scan data.

8. A method according to claim 1, wherein said radiation source is a cone-beam source.

9. A method according to claim 1, wherein the step of selecting at least one clear path data projection further includes the step of determining a linear dimension of said object along an axis defined by said clear path projection.

10. A method according to claim 9, wherein said step of recognizing said object further includes said linear dimension as a parameter of said function.

11. An apparatus for detecting an object in a region having a longitudinal axis, said object having at least a first physical characteristic and a second physical characteristic, said apparatus comprising:
   A. a radiation source alternately radiating at least at a first energy level and at a second energy level, and an array of detectors on opposed sides of said region, said radiation source being mounted on a rotatable member rotatable about said longitudinal axis of the region while said radiation source emits radiation toward said array of detectors, said array of detectors receiving radiation from said region to generate scan data for said region.

12. An apparatus according to claim 11, wherein said clear-path projection includes only said object.

13. An apparatus according to claim 11, wherein said projection computer includes programming so as to apply an Alvarez/Macovski algorithm to said first set of scan data and said second set of scan data by way of a computer system, so as to produce said first value and said second value.

14. An apparatus according to claim 11, wherein said array of detectors is also rotated about said longitudinal axis to scan said region.

15. An apparatus according to claim 11, wherein said data selection device further selects a second view angle for a second clear-path projection of said object, said second clear path projection being generated from said scan data generated during said scanning step.

16. An apparatus according to claim 11, wherein said data selection device further selects a plurality of additional view angles for a plurality of additional clear-path projections of the object, said plurality of additional clear-path projections being generated from said scan data generated by said array of detectors.

17. An apparatus according to claim 11, wherein said region is scanned with a computed tomography (CT) device to generate said scan data.

18. An apparatus according to claim 11, wherein said radiation source is a cone-beam source.

19. An apparatus according to claim 11, wherein said spatial analysis computer further determines a linear dimension of said object along an axis defined by said clear path projection.

20. An apparatus according to claim 19, wherein said projection computer further includes said linear dimension as a parameter of said function.

* * * * *

UNITED STATES PATENT AND TRADEMARK OFFICE
CERTIFICATE OF CORRECTION

PATENT NO. : 6,418,189 B1
DATED : July 9, 2002
INVENTOR(S) : David A. Schafer

It is certified that error appears in the above-identified patent and that said Letters Patent is hereby corrected as shown below:

Column 10,
Line 60, insert the following:

B. a reconstruction computer receiving a plurality of scan data projections obtained from a respective plurality of view angles from said scanning detectors, each of said plurality of view angles corresponding to said first energy level, each scan data projection containing scan data at its respective view angle, said reconstruction computer further defining at least one image data slice, each data slice corresponding to said first energy level, at a position along said longitudinal axis of said region;

C. a spatial analysis computer receiving said image data slice corresponding to said first energy level, wherein said spatial analysis computer selects at least one clear-path scan data projection corresponding to one of said view angles as a function of said image data slice corresponding to said first energy level, wherein said clear-path projection includes at least said object, and a data selection device receiving said sets of scan data and selecting a first set of scan data at said first energy level and a second set of scan data at said second energy level, each set of data corresponding to said clear-path projection;

D. a projection computer receiving said first set of scan data and said second set of scan data, corresponding to said clear-path scan data projection, and generating a first value representative of said first physical characteristic and a second value representative of said second physical characteristic, and recognizing and identifying said object as a function of said first value and said second value.

Signed and Sealed this

Third Day of June, 2003

JAMES E. ROGAN
*Director of the United States Patent and Trademark Office*